(12) United States Patent
Williams et al.

(10) Patent No.: US 10,898,121 B2
(45) Date of Patent: *Jan. 26, 2021

(54) EXERCISE APPARATUS SIMULATING MILD TO HIGH ALTITUDE ENVIRONMENTS

(71) Applicant: Stratosphere ATC LLC, Westlake Village, CA (US)

(72) Inventors: Robert Paul Williams, Westlake Village, CA (US); Bruce D. Johnson, Rochester, MN (US)

(73) Assignee: Stratosphere ATC LLC, Westlake Village, CA (US)

( * ) Notice: Subject to any disclaimer, the term of this patent is extended or adjusted under 35 U.S.C. 154(b) by 33 days.

This patent is subject to a terminal disclaimer.

(21) Appl. No.: 16/189,630

(22) Filed: Nov. 13, 2018

(65) Prior Publication Data

US 2019/0076076 A1 Mar. 14, 2019

Related U.S. Application Data

(63) Continuation of application No. 14/822,121, filed on Aug. 10, 2015, now Pat. No. 10,219,734.

(Continued)

(51) Int. Cl.
*A61B 5/22* (2006.01)
*A61G 10/02* (2006.01)
(Continued)

(52) U.S. Cl.
CPC .......... *A61B 5/222* (2013.01); *A61B 5/02055* (2013.01); *A61B 5/6888* (2013.01);
(Continued)

(58) Field of Classification Search
CPC ... A61B 5/02055; A61B 5/222; A61B 5/4857; A61B 5/6888; A61B 2503/10; A61G 10/02; A61G 10/023; A61G 10/026; A62B 31/00; A62B 21/0085; A62B 21/0088; A62B 22/0076; A62B 22/02; A62B 22/04; A62B 22/06; A62B 22/0605;
(Continued)

(56) References Cited

U.S. PATENT DOCUMENTS 4,974,829 A * 12/1990 Gamow ............... A61G 10/026
472/94
5,109,837 A * 5/1992 Gamow ............... A61G 10/026
128/200.24

(Continued)

*Primary Examiner* — Gary D Urbiel Goldner
(74) *Attorney, Agent, or Firm* — Sunstein LLP

(57) ABSTRACT

A personal physical conditioning system, for a single, full-size human subject, has a sealable chamber that is configured to allow entry therein and occupancy thereof by the entirety of the single, full-size human subject and to allow the subject to exercise in a standing position using an item of physical conditioning equipment entirely contained within the sealable chamber. The system also has a ventilation system, including a pump, operable to change air in the sealable chamber and to establish, within the sealable chamber, a desired non-zero air pressure level of less than 1 atmosphere and down to pressure conditions substantially equivalent to an elevation of 25,000 feet above sea level. Related methods are also provided.

20 Claims, 5 Drawing Sheets

Related U.S. Application Data

(60) Provisional application No. 62/035,630, filed on Aug. 11, 2014.

(51) Int. Cl.
*A62B 31/00* (2006.01)
*A61B 5/0205* (2006.01)
*A63B 22/02* (2006.01)
*A61B 5/00* (2006.01)
*A63B 22/06* (2006.01)
*A63B 22/00* (2006.01)
*A63B 71/00* (2006.01)
*A63B 23/00* (2006.01)

(52) U.S. Cl.
CPC .............. *A61G 10/02* (2013.01); *A62B 31/00* (2013.01); *A63B 22/02* (2013.01); *A61B 5/4857* (2013.01); *A61B 2503/10* (2013.01); *A63B 22/0056* (2013.01); *A63B 22/0076* (2013.01); *A63B 22/0605* (2013.01); *A63B 22/0664* (2013.01); *A63B 23/00* (2013.01); *A63B 2071/0081* (2013.01); *A63B 2208/056* (2013.01); *A63B 2213/005* (2013.01); *A63B 2220/75* (2013.01); *A63B 2225/20* (2013.01); *A63B 2225/50* (2013.01); *A63B 2230/062* (2013.01); *A63B 2230/208* (2013.01); *A63B 2230/425* (2013.01); *A63B 2230/505* (2013.01)

(58) Field of Classification Search
CPC ..... A62B 22/0664; A62B 22/14; A62B 22/16; A62B 23/00; A62B 23/035; A62B 23/03516; A62B 23/03525; A62B 23/03533; A62B 23/03541; A62B 23/04; A62B 23/0405; A62B 23/0476; A62B 23/0482; A62B 23/0494; A62B 23/12; A62B 23/1218; A62B 23/1245; A62B 23/1281; A62B 24/0062; A62B 24/0087; A62B 2024/0065; A62B 2024/009; A62B 2024/0093; A62B 69/0028; A62B 69/06; A62B 69/16; A62B 71/0054; A62B 2071/0081; A62B 2208/00; A62B 2208/05; A62B 2208/053; A62B 2208/056; A62B 2213/00; A62B 2213/005; A62B 2213/006; A62B 2220/70; A62B 2220/72; A62B 2220/73; A62B 2220/74; A62B 2220/75; A62B 2225/20; A62B 2225/50; A62B 2230/04; A62B 2230/045; A62B 2230/06; A62B 2230/062; A62B 2230/065; A62B 2230/067; A62B 2230/08; A62B 2230/085; A62B 2230/20; A62B 2230/201; A62B 2230/205; A62B 2230/206; A62B 2230/207; A62B 2230/208; A62B 2230/40; A62B 2230/405; A62B 2230/42; A62B 2230/425; A62B 2230/43; A62B 2230/431; A62B 2230/433; A62B 2230/435; A62B 2230/436; A62B 2230/438; A62B 2230/50; A62B 2230/505

See application file for complete search history.

(56) References Cited

U.S. PATENT DOCUMENTS

| | | | | |
|---|---|---|---|---|
| 5,133,339 | A * | 7/1992 | Whalen | A61H 9/005 128/202.12 |
| 5,356,361 | A * | 10/1994 | Watenpaugh | A63B 21/00181 482/111 |
| 5,360,001 | A * | 11/1994 | Brill | A61G 10/026 128/202.12 |
| 5,398,678 | A * | 3/1995 | Gamow | A61G 10/026 128/202.12 |
| 5,467,764 | A * | 11/1995 | Gamow | A61G 10/026 128/200.24 |
| 5,799,652 | A * | 9/1998 | Kotliar | A61G 10/00 128/200.24 |
| 5,860,857 | A * | 1/1999 | Wasastjerna | A61G 10/02 454/338 |
| RE36,958 | E * | 11/2000 | Gamow | A61G 10/026 128/200.24 |
| 6,508,850 | B1 * | 1/2003 | Kotliar | A61G 10/005 55/385.2 |
| 6,565,624 | B2 * | 5/2003 | Kutt | A61G 10/02 95/8 |
| 6,827,760 | B2 * | 12/2004 | Kutt | A61G 10/02 95/8 |
| 7,556,040 | B2 * | 7/2009 | Meyer | A61G 10/026 128/205.26 |
| 7,591,795 | B2 * | 9/2009 | Whalen | A63B 22/02 601/11 |
| 7,762,930 | B2 * | 7/2010 | Egger | A61H 1/0237 482/57 |
| 7,998,125 | B2 * | 8/2011 | Weston | A61M 1/008 52/2.18 |
| 8,375,938 | B2 * | 2/2013 | Gaumond | A61G 10/026 128/202.12 |
| 8,464,716 | B2 * | 6/2013 | Kuehne | A63B 21/00181 128/205.26 |
| 8,535,064 | B2 * | 9/2013 | Linton | A61G 10/026 128/202.12 |
| 8,739,792 | B2 * | 6/2014 | Holley | E04B 1/166 128/205.26 |
| 8,740,750 | B2 * | 6/2014 | Jerichow | A61B 5/0833 455/410 |
| 8,900,098 | B2 * | 12/2014 | Egan | A63B 21/00181 128/202.12 |
| 9,272,175 | B2 * | 3/2016 | Egan | A63B 22/06 |
| 9,421,331 | B2 * | 8/2016 | Linton | A61M 5/1723 |
| 10,219,734 | B2 * | 3/2019 | Williams | A61B 5/222 |
| 2002/0025889 | A1 * | 2/2002 | Egger | A61H 9/005 482/57 |
| 2007/0054783 | A1 * | 3/2007 | Egger | A61H 1/0237 482/57 |
| 2007/0181121 | A1 * | 8/2007 | Whalen | A63B 71/0054 128/202.12 |
| 2007/0184034 | A1 * | 8/2007 | Linton | A61K 38/193 424/93.7 |
| 2009/0217930 | A1 * | 9/2009 | Holley | E04B 1/3205 128/205.26 |
| 2011/0098157 | A1 * | 4/2011 | Whalen | A61H 9/00 482/52 |
| 2011/0098615 | A1 * | 4/2011 | Whalen | A61H 9/00 601/151 |
| 2011/0120567 | A1 * | 5/2011 | Kuehne | A63B 21/00181 137/14 |
| 2011/0226252 | A1 * | 9/2011 | Milne | A61G 10/023 128/205.26 |
| 2012/0152243 | A1 * | 6/2012 | Hingley | A61G 10/02 128/203.12 |

(56) References Cited

U.S. PATENT DOCUMENTS

| | | | |
|---|---|---|---|
| 2014/0014100 A1* | 1/2014 | Linton | A61G 10/026 128/202.12 |
| 2014/0235412 A1* | 8/2014 | Dailey | A63B 22/0056 482/57 |
| 2014/0274563 A1* | 9/2014 | Sheta | A63B 69/125 482/2 |
| 2016/0038071 A1* | 2/2016 | Williams | A61G 10/02 600/301 |

* cited by examiner

EXERCISE APPARATUS SIMULATING MILD TO HIGH ALTITUDE ENVIRONMENTS

CROSS-REFERENCE TO RELATED APPLICATION(S)

The present application is a continuation of U.S. application Ser. No. 14/822,121, filed on Aug. 10, 2015, which claims the benefit of U.S. Provisional Application No. 62/035,630, filed on Aug. 11, 2014, for an invention having the same title as above. Each of these applications is hereby incorporated herein by reference in its entirety.

FIELD OF THE INVENTION

The field of this invention relates generally to the field of exercise equipment, and more specifically toward an entire exercise environment that simulates mild to high altitude including exercise equipment and body monitoring systems.

DESCRIPTION OF THE PRIOR ART

In competitive athletics, there is the push to find an advantage over your opponent or merely to improve over one's own previous performance. One method that has become popular is exposing oneself to changes in altitude, either terrestrial or simulated in order to receive the physiological changes that come with acclimatization to the lower pressure and hypoxic environment. Graded hypobaric exposure creates a stimulus, presumably linked to hypoxic mechanisms, which result in significant gene expression and up-regulation of biochemical pathways, typically with improvements in oxygen delivery to tissues.

The currently adopted model for altitude exposure is to "live high and train low" (LHTL), where an athlete will live in a high altitude environment, either geographically or simulated and then train at a lower altitude. The environment of altitude brings the stimulus of low pressure, i.e., hypobaria which creates the low oxygen condition, i.e., hypoxia. Research has demonstrated that LHTL results in increases in VO2 max, i.e., measure of aerobic capacity, hemoglobin, i.e., red blood cells levels, circulating erythropoietin levels, lactate threshold and muscle buffering capacity. Additionally, it often improves performance as demonstrated in reduced time trial times and increased efficiency. For athletes that cannot travel to live in a high altitude location, many will sleep in tents supplied with low oxygen (e.g., 12% FiO2) to simulate the hypoxic condition of altitude known as normobaric hypoxia.

Interestingly, the opposite of high altitude is the environment of hyperbaria. High pressure treatment has been used extensively for wound healing in centers across the country, particularly in diabetics or those with other damaged tissue with poor blood supply. It is also used in individuals exposed to carbon monoxide or other toxins. The hyperbaric treatment has been thought to work primarily by driving oxygen deep into tissues. However, more recent evidence suggests some of the benefit may be due to the oscillations or change in pressure rather than just the higher oxygenation. Thus, some have suggested that some type of combination of hypobaric exposure combined with the stress associated with intermittent oscillations may result in additive benefits, particularly when it comes to athletic performance.

Historically however, intermittent exposure to lower oxygen levels, i.e., short-stays of hypobaric exposure or even normobaric hypoxia introduced in brief exposures has also been used as a treatment for asthma and other chronic illnesses. More recently it is being investigated for application for improving conditions such as heart failure. However, the majority of these so-called clinical claims come from older studies that were either not controlled or poorly controlled. Thus, more research needs to be done to determine the potential physiological benefits of varied types of hypobaric exposure in assorted populations with regard to frequency, duration and intensity of exposure.

Limited work with more sustained exposures of at least 6-8 hours over successive nights or days or even during mild exercise may alter breathing, stimulate a peripheral vasodilation, shift substrate utilization, increase erythropoietin, red cell mass, and myoglobin levels, and alter gene expression, circulating metabolites and immune function, somewhat similar to living at high altitude. Furthermore, this more limited exposure may stimulate receptors that influence fluid clearance mechanisms, particularly in the lungs, e.g., beta 2 adrenergic receptors as well as epithelial sodium channels. Thus, hypobaric treatment has extensive potential for benefitting human health and performance. Access to high altitude is not always feasible and unlike personal hypoxic tents to simulate the low oxygen of altitude, personal hypobaric chambers to simulate the low pressure hypoxic environment of altitude have not typically been commercially available. However, anecdotal and personal experience suggest promise in this area.

Prior art includes a small system that oscillates external pressure at various rates, thus potentially altering physiological processes, many of which as noted are still being studied. To date, the similar pressure oscillation systems have suggested the ability to reduce tissue edema, improve oxygenation, pre-acclimatize individuals, and potentially enhance athletic performance. These mini chambers are being sold as consumer devices and have been used in chiropractic and alternative health centers over the last 8 to 10 years.

It is the object of the present invention to provide a novel personal exercise apparatus that allows simultaneous simulation of mild to high altitude environments with novel algorithmically driven novel additional environmental stressors that may be pre-programmed or personally developed via physiological feedback during training.

It is yet another object of the instant invention to provide additional stressors that include the ability to transiently alter chamber pressure at variable frequencies and amplitudes with a range of step or ramp changes with the option of random pressure oscillations designed to personalize training programs.

It is yet another object of the instant invention to provide additional stressors that include small variations in inspired $CO_2$ levels and temperature allowing individuals to stimulate breathing and temperature conditions m preparation for desired environmental conditions.

It is yet another object of the instant invention to provide a chamber that is designed to allow maximal safety and comfort as well as an ergometric optimize design.

It is yet another object of the instant invention to provide a chamber that has an airflow system to allow rapid turnover of inspired air.

It is yet another object of the instant invention to provide a chamber that has temperature conditioning of the air.

It is yet another object of the instant invention to provide a chamber that has built-in analyzers to track $CO_2$ and $O_2$ levels wherein the $CO_2$ is modulated by a combination of reduced $CO_2$ turnover from expiration as well as reservoirs of compressed $CO_2$ gas.

It is yet another object of the instant invention to provide a chamber that can simulate altitude and is essentially a vacuum chamber that allows a range of pressure from sea level to the very limits of terrestrial altitude exposure, i.e., approximately 25,000 feet.

It is yet another object of the instant invention to provide a chamber programmed and designed for gradual and graded exposure over the course of weeks to months and that includes safety profiles that prevent rapid exposure to high altitudes in un-acclimatized subjects.

It is yet another object of the instant invention to prevent rapid exposure at rates faster than recommended by current altitude exposure charts.

SUMMARY OF THE INVENTION

The basic embodiment of the present invention teaches a system and apparatus for the improvement of exercise or athletic performance and recovery from physical stress comprising: an enclosed chamber sufficient for entry by a full size human; a pressure-altering apparatus to change the atmosphere inside of said chamber such that the pressure can be altered to simulate a change in elevation and corresponding gas concentrations; one or more pieces of exercise or recovery equipment placed in said chamber for use by a human; a monitoring system wherein the health status of said human is recorded and monitored before, during and after use of said system and apparatus; and an ability to apply external pressure patterns, wherein various periods and amplitudes of the pressure patterns can be individualized.

The above embodiment can be further modified by defining that said external pressure patterns are taken from the group comprising but not limited to: sine, saw tooth, square, triangle or other geometric patterns, randomized or combination of multiple waveforms.

The above embodiment can be further modified by defining that said exercise and recovery equipment is taken from the group comprising but not limited to: treadmill, cycle and arm ergometer, rowing machine, stair stepper, strength equipment, platform, zero-gravity chair.

The above embodiment can be further modified by defining that biorhythm and physiologic feedback is employed to vary the amount of pressure in said chamber.

The above embodiment can be further modified by defining that said biorhythm and physiologic feedback is employed to alter inspired $CO_2$ levels.

The above embodiment can be further modified by defining that said monitoring system measures data taken from but not limited to the following group: heart rate, breathing rate, skin temperature, oxygen saturation.

The above embodiment can be further modified by defining that said enclosed chamber is configured to remain bacteria free through the introduction of UV light set at 254 nm.

The above embodiment can be further modified by defining that negative ions are introduced into said chamber.

The above embodiment can be further modified by defining that said negative ions are adjusted for the altitude and oxygen present.

The above embodiment can be further modified by defining that said negative ions are decreased as the altitude goes down thereby increasing the density of negative ions due to the increased volume of air in said chamber.

The above embodiment can be further modified by defining that a HEPA filter is used to filter the air wherein said HEPA filter removes particles down to 93 microns thereby keeping dust and other particulates out of said chamber.

The above embodiment can be further modified by defining that said UV light at 254 nm is augmented with a titanium dioxide filter thereby increasing the intensity of said UV light by 40 times thereby ensuring that all bacteria and germs in said chamber are eliminated.

The above embodiment can be further modified by defining that a plasma grid of high voltage wires is used thereby providing a positive and negative grid that will attract dust and remove bacteria.

The above embodiment can be further modified by defining that a combination of a HEPA filter and UV light with titanium dioxide plasma grid is used in a manner that allows the volume of air flow in said chamber to change every 3 minutes.

The above embodiment can be further modified by defining that said system is wirelessly connected to the cloud thereby allowing for data capture and providing coaching feedback in order to individualize training and exposure programs.

The above embodiment can be further modified by defining that a range of oscillatory patterns that span the known resonant frequencies of the human body of 0 to 30 Hz with the pressure oscillation ranges of 0 to 150 mm Hg is allowed.

The instant invention teaches a personal hypobaric chamber ergometrically designed for small spaces, optimized personal safety and for optimized exercise activity.

BRIEF DESCRIPTION OF THE DRAWINGS

For a better understanding of the present invention, reference is to be made to the accompanying drawings. It is to be understood that the present invention is not limited to the precise arrangement shown in the drawings.

DETAILED DESCRIPTION OF A PREFERRED EMBODIMENT

Figure 1:
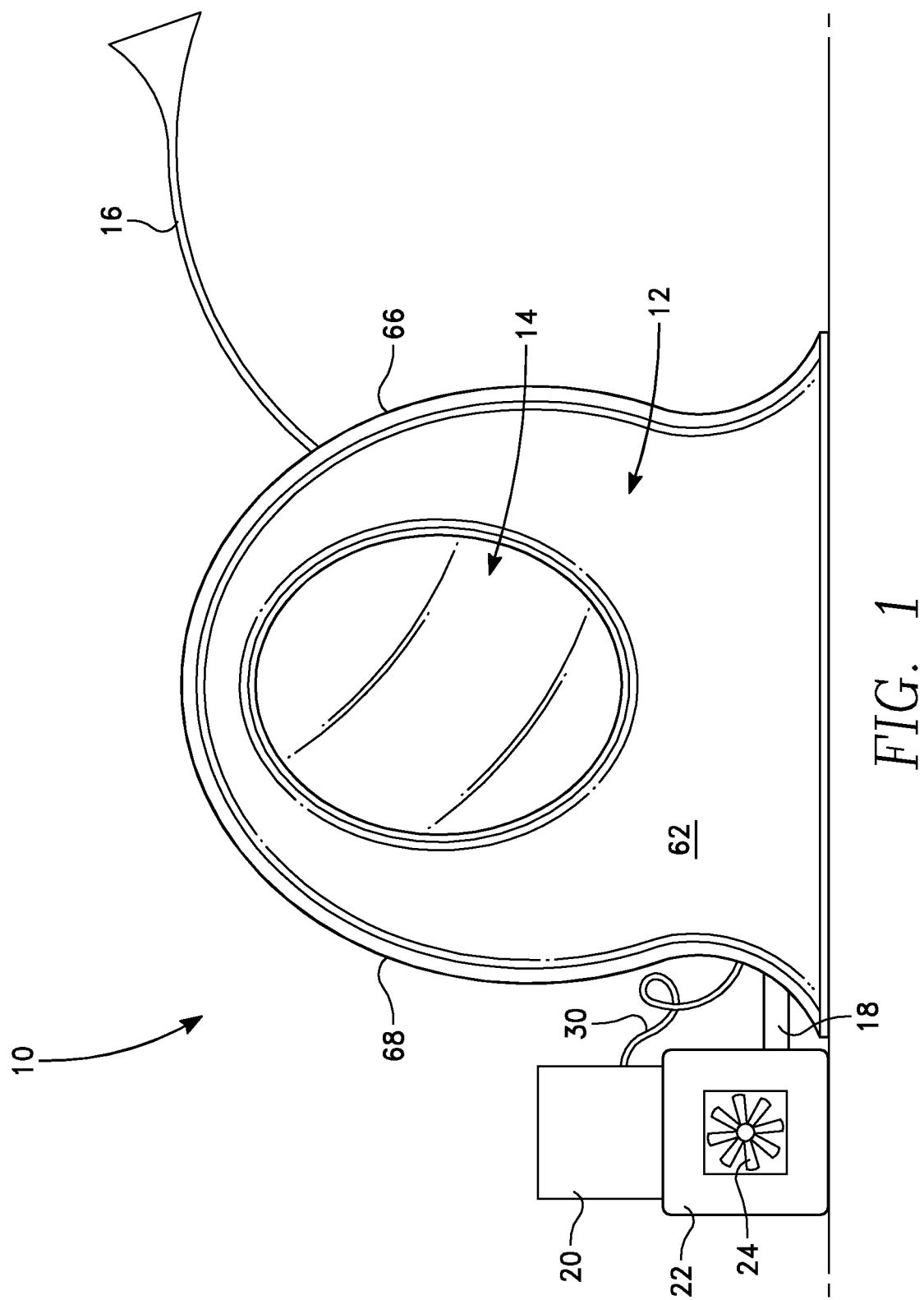
FIG. 1 shows a side view of the exercise apparatus of the instant invention with the access door open.

Turning to the drawings, the preferred embodiment is illustrated and described by reference characters that denote similar elements throughout the several views of the instant invention.

The preferred embodiment provides for a personal consumer-based, novel personal exercise apparatus 10 that allows simultaneous simulation of mild to high altitude environments and algorithmically driven novel additional environmental stressors that may be pre-programmed or personally developed via physiological feedback during training. Additional stressors include the ability to transiently alter chamber pressure at variable frequencies and amplitudes with a range of step or ramp changes with the option of random pressure oscillations designed to personalize/optimize training programs. Additional stressors include small variations in inspired $CO_2$ levels and temperature allowing individuals to stimulate breathing and temperature conditions in preparation for desired environmental conditions. The chamber is designed to allow maximal safety and comfort as well as ergometrically optimized design. The chamber has an airflow system to allow rapid turnover of inspired air, temperature conditioning of the air between 40 and 90 degrees F., and has built in analyzers to track $CO_2$ and $O_2$ levels. $CO_2$ is modulated by a combination of reduced $CO_2$ turn over from exhaled air of the user as well as reservoirs of compressed $CO_2$ gas. To simulate altitude, the chamber is essentially a vacuum chamber that allows a range of pressure from sea level to the very limits of terrestrial altitude exposure, i.e., approximately 25,000 feet. Programs are designed for gradual and graded exposure over the course of weeks to months and safety profiles prevent rapid exposure to high altitudes in un-acclimatized subjects. Rapid exposure in acclimatized subjects at rates faster than recommended by current altitude exposure charts is also prevented.

Turning to FIG. 1, the preferred embodiment is shown wherein the exercise apparatus 10 has an ergonomically shaped outer shell 12 with a first side 62, a second side 64 (seen in FIGS. 2-3), a door side 66 and a back side 68. The preferred embodiment has a curved outer shell 12 but it is understood that multiple shapes are contemplated and this apparatus is not limited to the outer shape shown in the preferred embodiment. The door side 66 aptly has a door 16 to allow entry into the controlled interior portion 38 as well as sealing for the introduction of controlled pressure and gas levels, such as oxygen and carbon dioxide. The first side 62 and the second side 64 each have a window 14, 14A, 14B to allow the user 32 inside to see out and for observers outside to see in. A door window 26 and a back door window 28 are also optionally included. The interior portion 38 is connected through a connector 18 to a controller 20 and a vacuum/compressor combination 22, 22A, 22B to allow for the control of the pressure inside of the interior portion 38 of the exercise apparatus 10.

Figure 3:
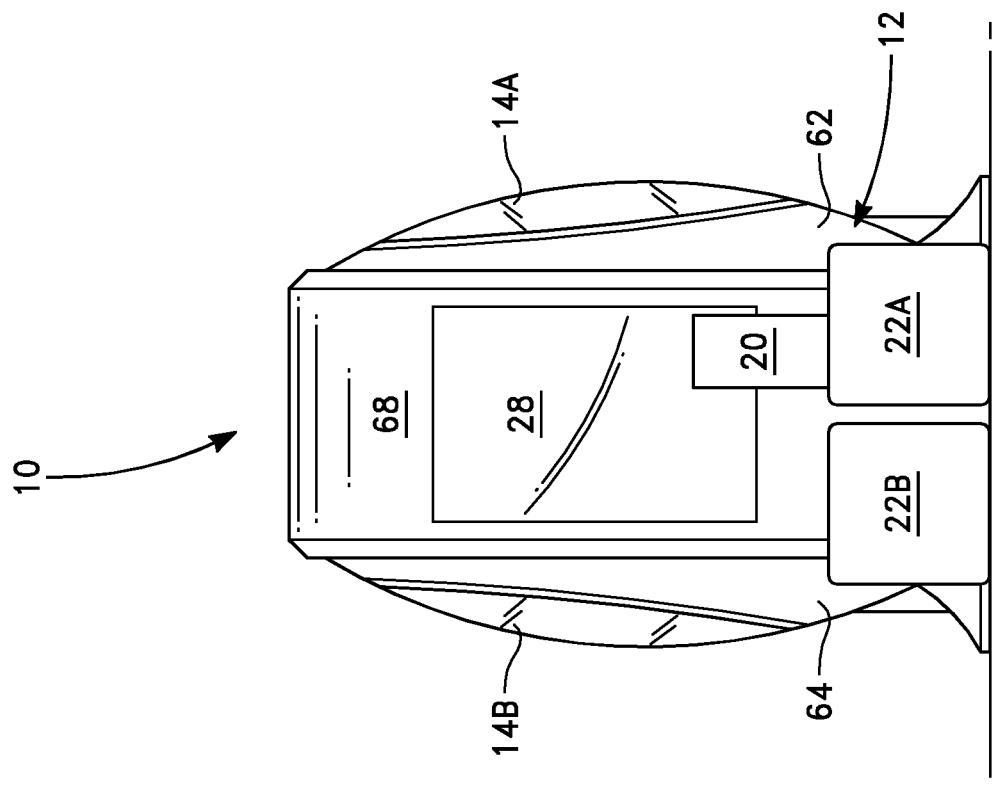
FIG. 3 is a second non-door side view of the exercise apparatus of the instant invention with the access door closed.
Figure 2:
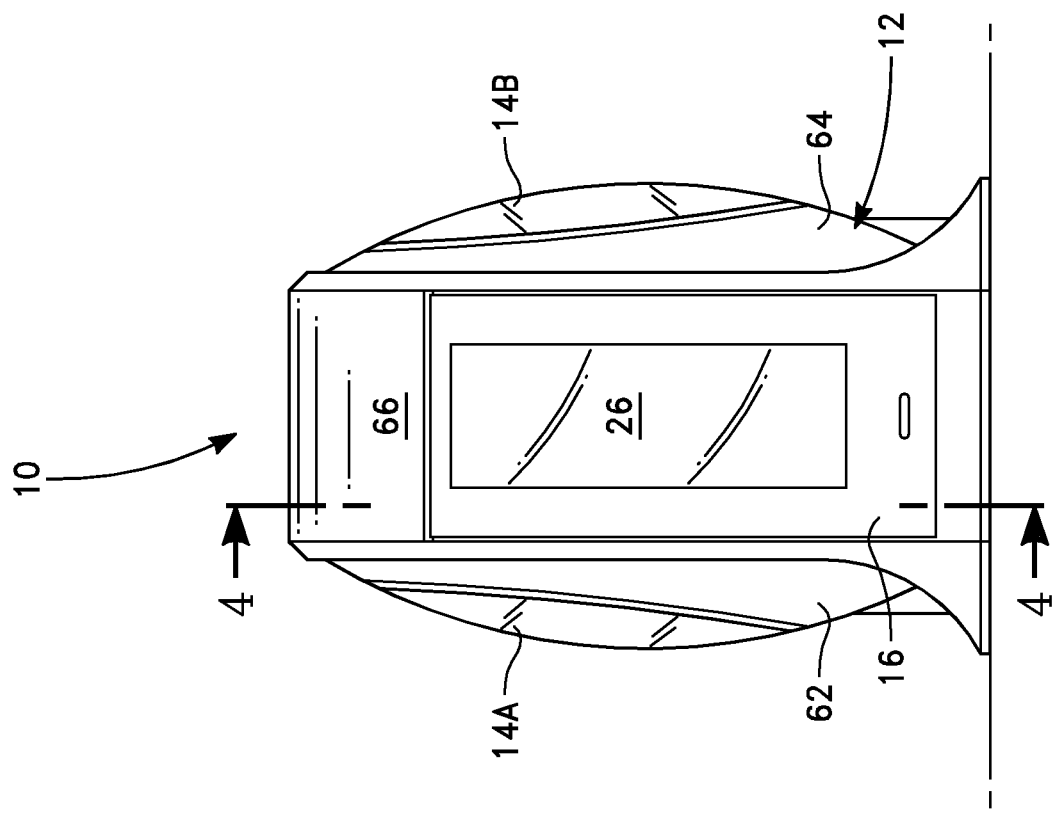
FIG. 2 shows a first door side view of the exercise apparatus of the instant invention with the access door closed.

The sides of the invention are shown in FIGS. 2-3. The back side 68 (where the door 16 is not) includes the connections to the controller 20 and pressure/vacuum supplying machines 22A, 22B. The door side 66 aptly has the door 16 that opens in a vertical direction in this embodiment.

Figure 4:
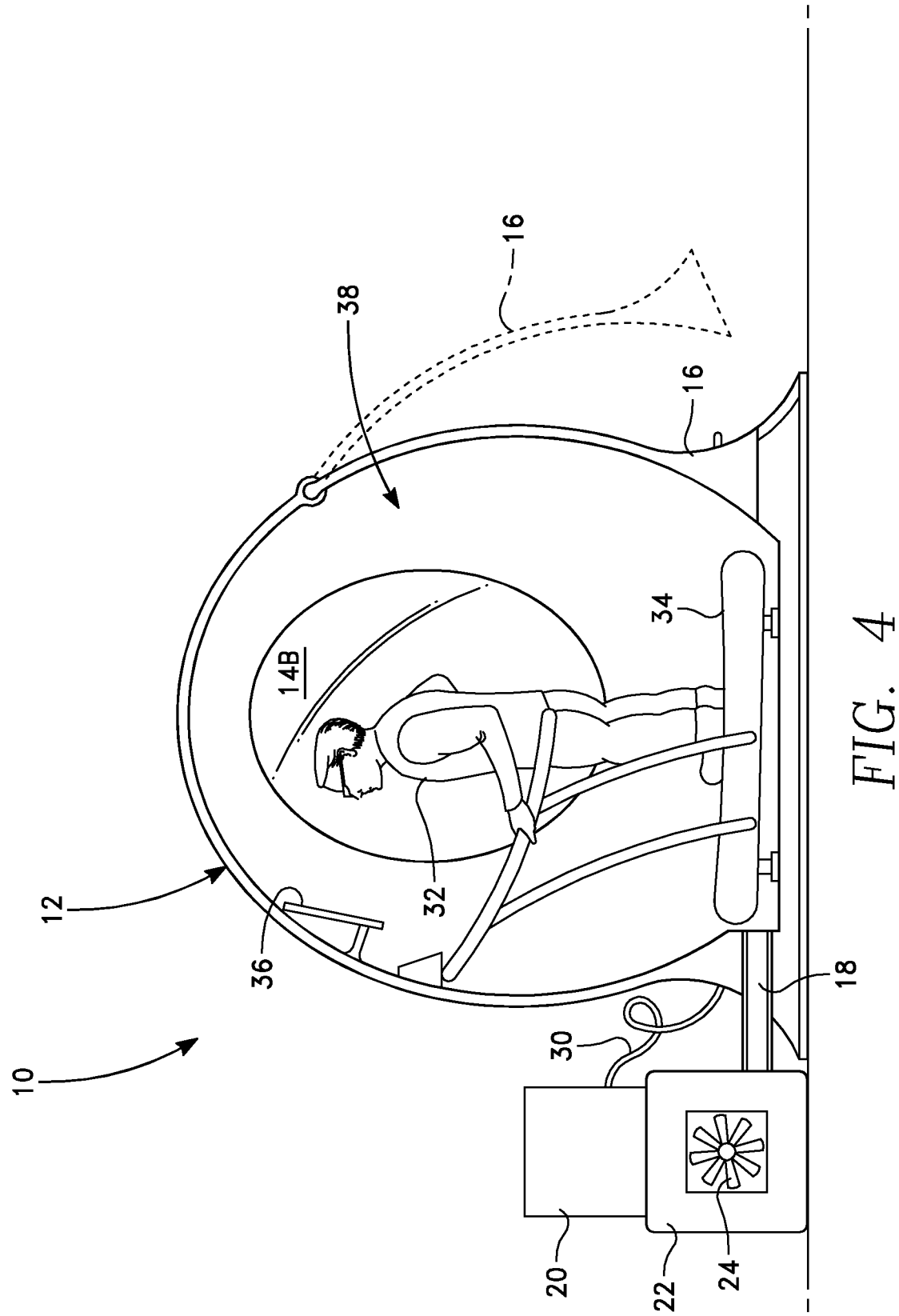
FIG. 4 is taken along the cross-sectional line 4-4 in FIG. 2.

As seen in FIG. 4, which is a cut out of the first side of the exercise machine 10, the user 32 is sealed into the interior portion 38 of the exercise machine 10 when the door 16 is sealed shut. The user avails him or herself of an exercise machine 34 found therein. As illustrated, the exercise machine is a treadmill, but it is contemplated that any exercise machine found in any exercise environment could be placed into the interior portion 38 of the exercise apparatus 10 of the instant invention. It is not limited to a treadmill, which is shown for illustrative purposes only. There is an interior monitor 36 for the user 32 to access and there is of course the window 14B to the second side which the user can look through or observes can observe through.

Figure 5:
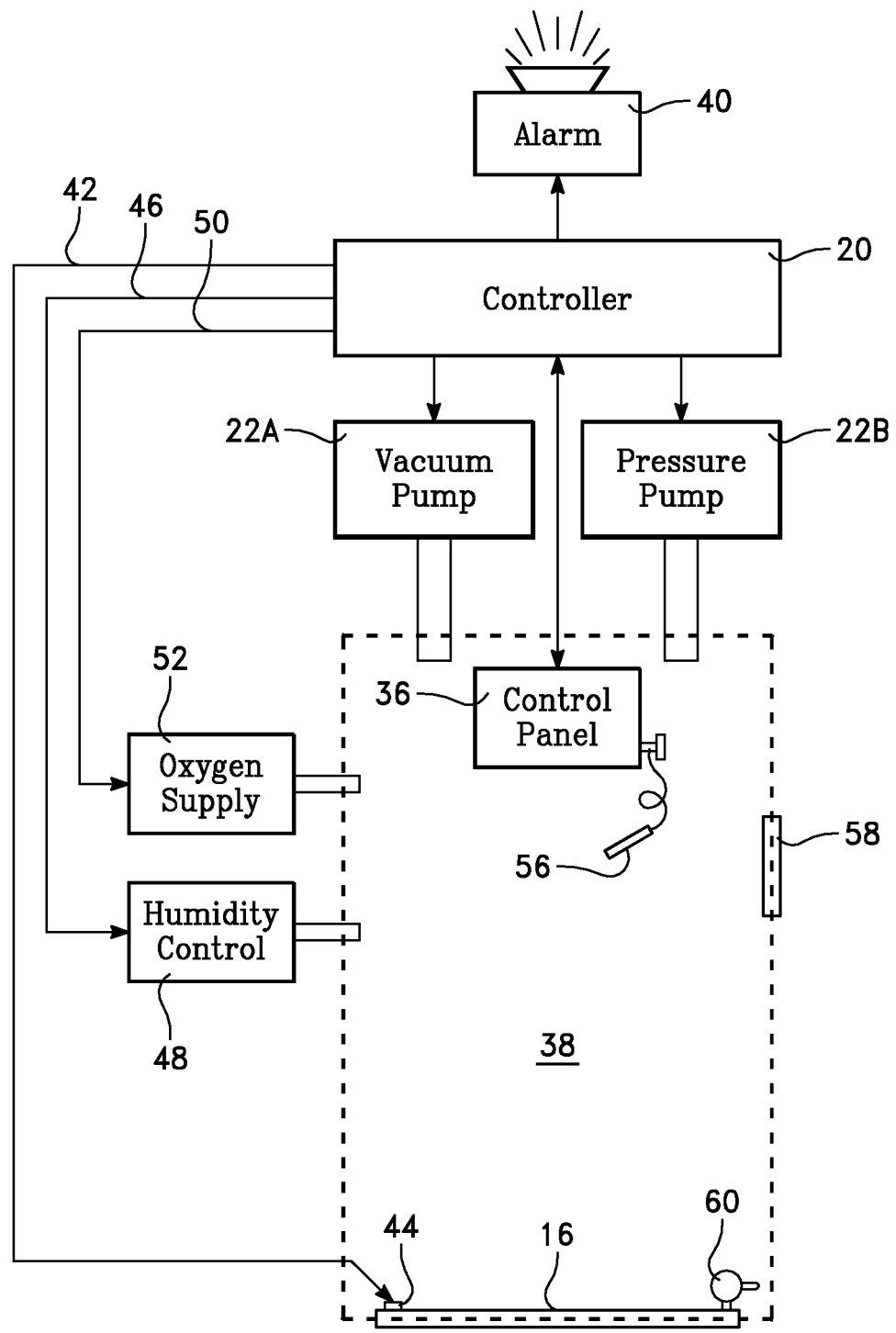
FIG. 5 is a block diagram of the system of use of the exercise apparatus of the instant invention.

The connector 20 is connected to a power source through an electrical connector 30 and it is also connected to the interior portion 38 of the exercise apparatus 10 through a series of connectors 18 which are further defined in the block diagram of FIG. 5.

The controller 20 has a first connection 42 to the door release 44 to allow the door 16 to open and close. A second connection 46 connects the controller 20 to the humidity controls 48 into the interior portion 38 of the exercise apparatus 10. A third connection 50 connects the controller 20 to the oxygen and/or carbon dioxide supply 52 into the interior portion 38 of the exercise apparatus 10. The controller 20 also is in connected communication with a vacuum pump 22A and a pressure pump/compressor 22B to control the pressure inside the interior portion 38 of the exercise apparatus 10. The interior portion 38 of the exercise apparatus 10 also includes a manual door release 60 and a manual emergency hatch 58 should the apparatus 10 need to be opened for the well-being of the user 32 therein and the automatic controls are otherwise unavailable due to malfunction or emergency. Inside the interior portion 38 of the exercise apparatus 10 is the control panel 54 that is utilized by the user 32 and is in communication with the internal monitor 36 found therein. There is a wrist strap 56 for the user 32 to wear should an emergency occur and the user falls or faints. In such an event, the wrist-strap 56 would disconnect from the user 32, thereby powering down the exercise apparatus 10, opening the door 16 and sounding the alarm 40.

Figure 6:
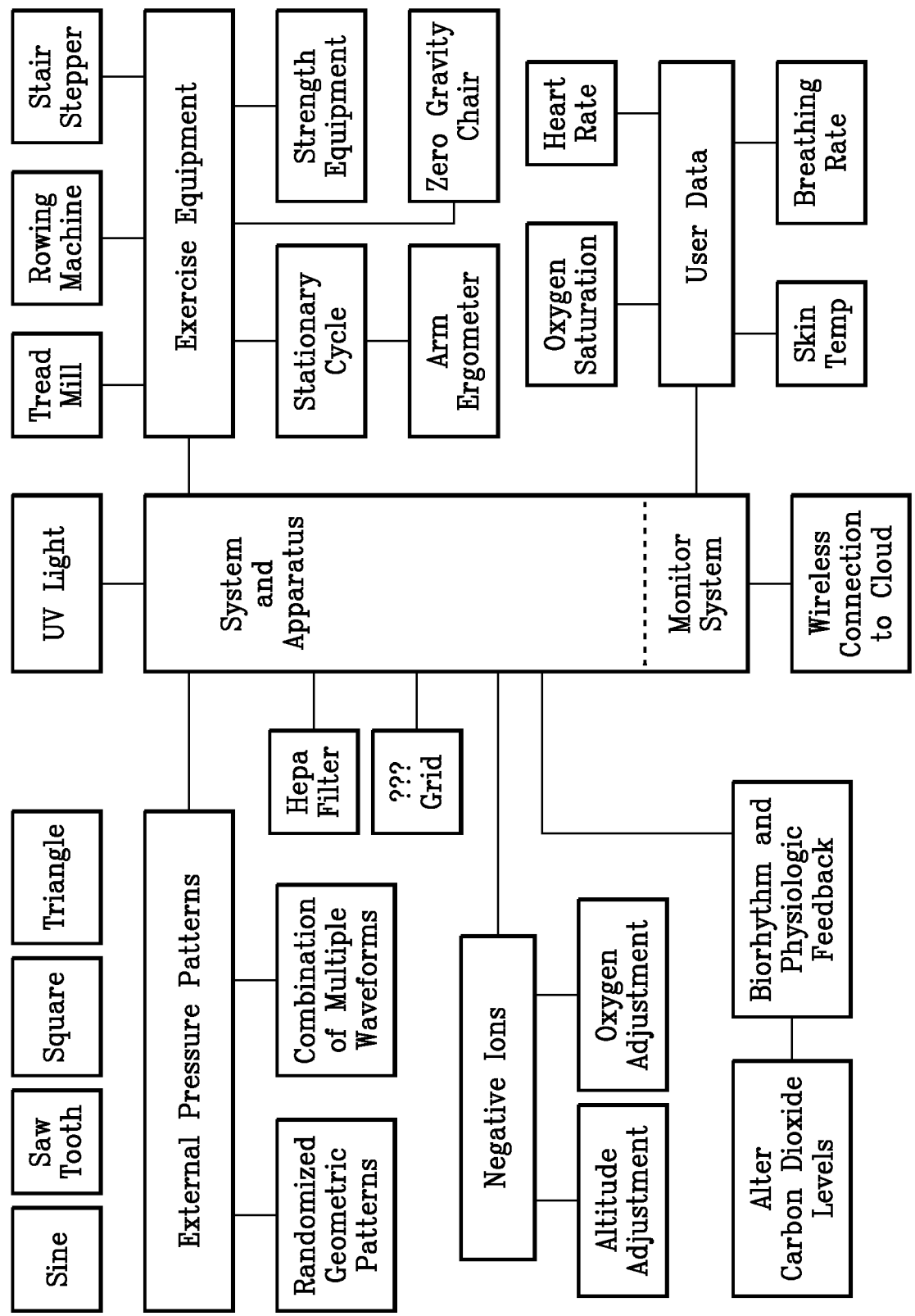
FIG. 6 is a block diagram of the physical and controlling inputs into the apparatus and system of the instant invention.

FIG. 6 shows in block diagram form that physical and controlling inputs that can be applied to the system and apparatus of the instant invention.

The discussion included in this patent is intended to serve as a basic description. The reader should be aware that the specific discussion may not explicitly describe all embodiments possible and alternatives are implicit. Also, this discussion may not fully explain the generic nature of the invention and may not explicitly show how each feature or element can actually be representative or equivalent elements. Again, these are implicitly included in this disclosure. Where the invention is described in device-oriented terminology, each element of the device implicitly performs a function. It should also be understood that a variety of changes may be made without departing from the essence of the invention. Such changes are also implicitly included in the description. These changes still fall within the scope of this invention.

Further, each of the various elements of the invention and claims may also be achieved in a variety of manners. This disclosure should be understood to encompass each such variation, be it a variation of any apparatus embodiment, a method embodiment, or even merely a variation of any element of these. Particularly, it should be understood that as the disclosure relates to elements of the invention, the words for each element may be expressed by equivalent apparatus terms even if only the function or result is the same. Such equivalent, broader, or even more generic terms should be considered to be encompassed in the description of each element or action. Such terms can be substituted where desired to make explicit the implicitly broad coverage to which this invention is entitled. It should be understood that all actions may be expressed as a means for taking that action or as an element which causes that action. Similarly, each physical element disclosed should be understood to encompass a disclosure of the action which that physical element facilitates. Such changes and alternative terms are to be understood to be explicitly included in the description.

What is claimed is:

1. A personal physical conditioning system for a single, full-size human subject, the personal physical conditioning system comprising:

a sealable chamber, the sealable chamber configured to allow entry therein and occupancy thereof by an entirety of the single, full-size human subject and to allow the single, full-size human subject to exercise in a standing position using an item of physical conditioning equipment entirely contained within the sealable chamber;

a ventilation system, including a pump, operable to change air in the sealable chamber and to establish, within the sealable chamber, a desired non-zero air pressure level of less than 1 atmosphere and down to pressure conditions substantially equivalent to an elevation of 25,000 feet above sea level;

a monitoring system operable to monitor vital signs of the single, full-size human subject, the vital signs including at least one parameter selected from the group consisting of heart rate, breathing rate, skin temperature, oxygen saturation, and combinations thereof; and a controller coupled to the ventilation system and operable to regulate air pressure in the sealable chamber at the desired non-zero air pressure level under specifiable conditions;

wherein the sealable chamber has a size and shape for use in an interior space and wherein the monitoring system is configured to monitor the vital signs of the single, full-size human subject while the entirety of the single, full-size human subject is in the sealable chamber.

2. The personal physical conditioning system according to claim 1, wherein the controller is configured to regulate the air pressure in the sealable chamber under the specifiable conditions that include a pattern of modulation of the air pressure within the sealable chamber.

3. The personal physical conditioning system according to claim 2, wherein the pattern of modulation by which the controller is configured to regulate the air pressure in the sealable chamber is determined at least in part based on the monitored vital signs of the single, full-size human subject.

4. The personal physical conditioning system according to claim 1, wherein the personal physical conditioning system is configured to allow a volume of air flow in the sealed chamber to change every three minutes.

5. The personal physical conditioning system according to claim 1, further comprising a light configured to destroy bacteria poised to occupy the sealable chamber.

6. The personal physical conditioning system according to claim 1, wherein the personal physical conditioning system is configured to introduce negative ions into the sealable chamber.

7. The personal physical conditioning system according to claim 1, further comprising a HEPA filter that filters the air within the sealable chamber.

8. The personal physical conditioning system according to claim 7, further comprising a light configured to destroy bacteria poised to occupy the sealable chamber.

9. The personal physical conditioning system according to claim 1, wherein the monitoring system is coupled to a cloud network configured to capture data processed by the monitoring system and to individualize training.

10. The personal physical conditioning system according to claim 1, wherein the item of physical conditioning equipment is selected from the group consisting of a treadmill, a cycle and arm ergometer, a rowing machine, a stair stepper, strength equipment, and a zero-gravity chair.

11. A method of personal physical conditioning comprising:
    entering, by the single, full-size human subject, the personal physical conditioning system of claim 1, into which has placed the item of physical conditioning equipment;
    using the controller to regulate the air pressure in the sealable chamber at the desired non-zero air pressure level below 1 atmosphere; and
    while the single, full-size human subject and the item of physical conditioning equipment are entirely contained in the sealable chamber, using, by the single, full-size human subject, the item of physical conditioning equipment.

12. The method of personal physical conditioning according to claim 11, wherein the controller is configured to regulate the air pressure in the sealable chamber under the specifiable conditions that include a pattern of modulation of the air pressure within the sealable chamber.

13. The method of personal physical conditioning according to claim 12, wherein the pattern of modulation by which the controller is configured to regulate the air pressure in the sealable chamber is determined at least in part based on the monitored vital signs of the single full-size human subject.

14. The method of personal physical conditioning according to claim 11, wherein the personal physical conditioning system is configured to allow a volume of air flow in the sealed chamber to change every three minutes.

15. The method of personal physical conditioning according to claim 11, wherein the personal physical conditioning system further comprises a light configured to destroy bacteria poised to occupy the sealable chamber.

16. The method of personal physical conditioning according to claim 11, wherein the personal physical conditioning system is configured to introduce negative ions into the sealable chamber.

17. The method of personal physical conditioning according to claim 11, wherein the personal physical conditioning system further comprises a HEPA filter that filters the air within the sealable chamber.

18. The method of personal physical conditioning according to claim 11, wherein the personal physical conditioning system further comprises a light configured to destroy bacteria poised to occupy the sealable chamber.

19. The method of personal physical conditioning according to claim 11, wherein the monitoring system is coupled to a cloud network configured to capture data processed by the monitoring system and to individualize training.

20. The method of personal physical conditioning according to claim 11, wherein the item of physical conditioning equipment is selected from the group consisting of a treadmill, a cycle and arm ergometer, a rowing machine, a stair stepper, strength equipment, and a zero-gravity chair.

* * * * *